US012773281B2

(12) United States Patent
Kang et al.

(10) Patent No.: US 12,773,281 B2
(45) Date of Patent: Oct. 27, 2026

(54) ROBOT ARM AND TRANSFER APPARATUS INCLUDING THE SAME

(71) Applicants: Samsung Display Co., Ltd., Yongin-si (KR); KCTECH CO., LTD., Anseong-si (KR)

(72) Inventors: Yunku Kang, Asan-si (KR); Jun Ho Kang, Anseong-si (KR); Eun Ho Park, Hwaseong-si (KR); Sungmin Park, Cheonan-si (KR)

(73) Assignees: SAMSUNG DISPLAY CO., LTD., Gyeonggi-Do (KR); KCTECH CO., LTD., Anseong-Si (KR)

( * ) Notice: Subject to any disclaimer, the term of this patent is extended or adjusted under 35 U.S.C. 154(b) by 911 days.

(21) Appl. No.: 18/074,806

(22) Filed: Dec. 5, 2022

(65) Prior Publication Data

US 2023/0225807 A1 Jul. 20, 2023

(30) Foreign Application Priority Data

Jan. 17, 2022 (KR) ........................ 10-2022-0006531

(51) Int. Cl.
*A61B 34/30* (2016.01)

(52) U.S. Cl.
CPC ........ *A61B 34/30* (2016.02); *A61B 2034/306* (2016.02)

(58) Field of Classification Search
CPC ............... A61B 34/30; A61B 2034/306; B25J 15/0033; B25J 15/0253; B25J 15/0616; B25J 15/0095; B25J 15/0075; B65G 47/91; B65G 49/061; B65G 2207/08; B65G 2207/40
See application file for complete search history.

(56) References Cited

U.S. PATENT DOCUMENTS

| | | | | |
|---|---|---|---|---|
| 6,010,516 A | 1/2000 | Hulka | | |
| 7,014,235 B1 * | 3/2006 | Ostwald | B25J 9/1612 | 901/38 |
| 7,422,411 B2 * | 9/2008 | Downs | B65G 47/90 | 414/730 |
| 8,690,213 B2 * | 4/2014 | Harada | B25J 15/026 | 901/32 |

(Continued)

FOREIGN PATENT DOCUMENTS

| | | |
|---|---|---|
| CN | 1787954 A | 6/2006 |
| CN | 103620415 A | 3/2014 |

(Continued)

*Primary Examiner* — Stephen A Vu
(74) *Attorney, Agent, or Firm* — CANTOR COLBURN LLP

(57) ABSTRACT

A robot arm includes a first hand, a second hand, and a distance adjusting part for adjusting a distance between the first hand and the second hand. The first hand includes a first body portion and a plurality of first protruding portions protruded from the first body portion to a second direction and arranged in a first direction crossing the second direction. The second hand includes a second body portion and a plurality of second protruding portions protruded from the second body portion to the second direction and arranged in the first direction. The first protruding portions and the second protruding portions are disposed between the first body portion and the second body portion.

20 Claims, 13 Drawing Sheets

(56) References Cited

U.S. PATENT DOCUMENTS

| | | | | |
|---|---|---|---|---|
| 8,752,873 | B2 * | 6/2014 | Hajrovic | B25J 15/0206 294/203 |
| 8,899,649 | B2 * | 12/2014 | Li | B25J 15/0028 294/902 |
| 9,004,560 | B2 * | 4/2015 | Umeno | B66C 1/42 901/31 |
| 9,108,320 | B2 | 8/2015 | Furuichi | |

FOREIGN PATENT DOCUMENTS

| | | | |
|---|---|---|---|
| CN | 113460728 | A | 10/2021 |
| JP | 4761334 | B2 | 8/2011 |
| JP | 5161335 | B2 | 3/2013 |
| JP | 5776772 | B2 | 7/2015 |
| KR | 20110131457 | A | 12/2011 |
| KR | 20150006376 | A | 1/2015 |
| KR | 1020160101733 | A | 8/2016 |
| KR | 1020160128031 | A | 11/2016 |
| KR | 102154685 | B1 | 9/2020 |
| KR | 102154686 | B1 | 9/2020 |

* cited by examiner

ROBOT ARM AND TRANSFER APPARATUS INCLUDING THE SAME

This application claims priority to Korean Patent Application No. 10-2022-0006531, filed on Jan. 17, 2022, and all the benefits accruing therefrom under 35 U.S.C. § 119, the content of which in its entirety is herein incorporated by reference.

BACKGROUND

1. Field of Disclosure

The present disclosure relates to a robot arm for transferring a window and a transfer apparatus including the robot arm.

2. Description of the Related Art

A robot arm transfers a window. The robot arm includes a robot hand, and the robot hand suctions the window to be adhered thereto using vacuum holes. The robot hand is changed depending on a transfer target to be transferred. The robot hand is replaced according to a size of the transfer target to be transferred.

SUMMARY

The present disclosure provides a robot arm capable of improving an efficiency of production equipment.

The present disclosure provides a transfer apparatus including the robot arm.

Embodiments of the invention provide a robot arm including a first hand, a second hand, and a distance adjusting part for adjusting a distance between the first hand and the second hand. The first hand includes a first body portion extending in a first direction and a plurality of first protruding portions protruded from the first body portion to a second direction crossing the first direction and arranged in the first direction. The second hand includes a second body portion extending in the first direction and a plurality of second protruding portions protruded from the second body portion to the second direction and arranged in the first direction. The first protruding portions and the second protruding portions are disposed between the first body portion and the second body portion.

The first protruding portions may be alternately arranged one by one with the second protruding portions in the first direction when the distance between the first body portion and the second body portion is a minimum distance.

The first hand may define a plurality of first vacuum holes therein, and the second hand may define a plurality of second vacuum holes therein.

The first body portion may include a first engraved pattern that is defined therein, the first engraved pattern may not overlap the first vacuum holes in a plan view, and may extend in the first direction, the second body portion may include a second engraved pattern that is defined therein, and the second engraved pattern may not overlap the second vacuum holes, and may extend in the first direction.

Each of the first hand and the second hand may include a third engraved pattern that is defined therein, and the third engraved pattern may not overlap the first vacuum holes and the second vacuum holes in the plan view, and may extend in the second direction.

The third engraved pattern may have a width of about 20 millimeters (mm) in the first direction.

Each of first portions of the first hand and the second hand that overlaps the first, second, and third engraved patterns in the plan view may have a thickness different from a thickness of each of second portions of the first hand and the second hand that does not overlap the first, second, and third engraved patterns in the plan view.

The robot arm may further include an auxiliary member disposed between the first hand and the second hand.

The auxiliary member may include a magnetic material, and the auxiliary member may be attachable to and detachable from the first hand and the second hand.

The auxiliary member may include a fourth engraved pattern defined therein and extending in the first direction.

The fourth engraved pattern may have a width of about 20 mm in the second direction.

The distance adjusting part may include: a transfer part, which adjusts the distance between the first hand and the second hand, and a fixing part, which fixes a position of the first hand and a position of the second hand.

The distance adjusting part may further include a setting member, which provides a reference of the distance between the first hand and the second hand, and the setting member is attachable and detachable.

The transfer part may include a first guide part and a second guide part spaced apart from the first guide part, and the first hand and the second hand may be coupled to the first guide part and the second guide part.

Each of the first hand and the second hand may include a coating layer including a fluororesin.

The robot arm further may include a sensor part disposed to overlap a hole defined through the second hand and which senses a transfer target.

The robot arm may further include a foreign substance cover member disposed between the first hand and the distance adjusting part and between the second hand and the distance adjusting part.

Embodiments of the invention provide a transfer apparatus including: a robot arm, which vacuum-suctions a window; and a joint part connected to the robot arm. The robot arm includes: a first hand including a first body portion extending in a first direction and a plurality of first protruding portions protruded from the first body portion to a second direction crossing the first direction and arranged in the first direction; a second hand including a second body portion extending in the first direction and a plurality of second protruding portions protruded from the second body portion to the second direction and arranged in the first direction; and a distance adjusting part, which adjusts a distance between the first hand and the second hand. The first protruding portions and the second protruding portions are disposed between the first body portion and the second body portion.

The transfer apparatus may further include an auxiliary member disposed between the first hand and the second hand.

The first body portion may include a first engraved pattern that is defined therein, the first engraved pattern may not overlap a plurality of first vacuum holes in a plan view, and may extend in the first direction, the second body portion may include a second engraved pattern that is defined therein, the second engraved pattern may not overlap a plurality of second vacuum holes in the plan view, and may extend in the first direction, each of the first hand and the second hand may include a third engraved pattern that is defined therein, the third engraved pattern may not overlap the first vacuum holes and the second vacuum holes, and may extend in the second direction, and the auxiliary member may include a fourth engraved pattern defined therein and extending in the first direction.

According to the above, the robot arm that includes the first hand and the second hand is able to transfer the window in various sizes by adjusting the distance between the first hand and the second hand without replacing the robot arm. As there is no need to replace the robot arm, a manufacturing cost for an additional robot arm, a time consumed to manufacture the additional robot arm, and a time required to replace the robot arm are reduced. Accordingly, a production equipment efficiency increases.

In addition, since the robot arm includes the first engraved pattern and the second engraved pattern, which are respectively defined in the first hand and the second hand, a residual pressure generated during a process of vacuum suctioning using the vacuum holes is discharged. Accordingly, a vacuum non-separation phenomenon is minimized, a static electricity is reduced, and defects such as cracks are effectively reduced in the window.

The third engraved pattern defined in the first and second hands and the fourth engraved pattern defined in the auxiliary member allow the folding area of the window not to make contact with the first hand, the second hand, and the auxiliary member when the window is being transferred. Accordingly, defects occurring in the folding area of the window are effectively reduced or prevented.

BRIEF DESCRIPTION OF THE DRAWINGS

The above and other advantages of the present disclosure will become readily apparent by reference to the following detailed description when considered in conjunction with the accompanying drawings wherein.

DETAILED DESCRIPTION

Figure 1A:
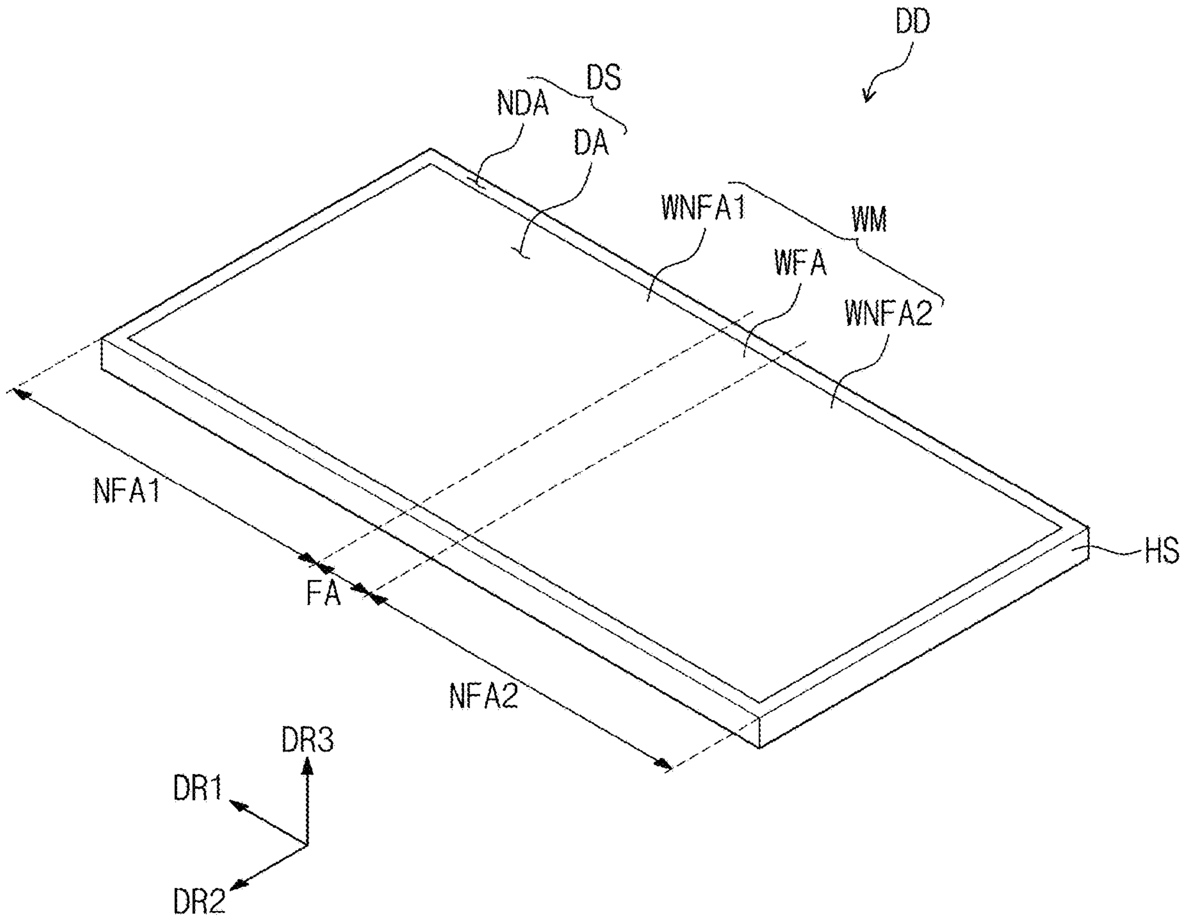
FIG. 1A is a perspective view of a display device according to an embodiment of the present disclosure.

In the present disclosure, it will be understood that when an element (or area, layer, or portion) is referred to as being "on", "connected to" or "coupled to" another element or layer, it can be directly on, connected or coupled to the other element or layer or intervening elements or layers may be present.

Like numerals refer to like elements throughout. In the drawings, the thickness, ratio, and dimension of components are exaggerated for effective description of the technical content. As used herein, the term "and/or" may include any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the teachings of the present disclosure. As used herein, the singular forms, "a", "an" and "the" are intended to include the plural forms as well, unless the context clearly indicates otherwise.

Spatially relative terms, such as "beneath", "below", "lower", "above", "upper" and the like, may be used herein for ease of description to describe one element or feature's relationship to another elements or features as shown in the figures.

It will be further understood that the terms "include" and/or "including", when used in this specification, specify the presence of stated features, integers, steps, operations, elements, and/or components, but do not preclude the presence or addition of one or more other features, integers, steps, operations, elements, components, and/or groups thereof.

The term "part" or "unit" as used herein is intended to mean a software component or a hardware component that performs a specific function. The hardware component may include, for example, a field-programmable gate array ("FPGA") or an application-specific integrated circuit ("ASIC"). The software component may refer to an executable code and/or data used by the executable code in an addressable storage medium.

Thus, the software components may be, for example, object-oriented software components, class components, and task components, and may include processes, functions, attributes, procedures, subroutines, segments of program code, drivers, firmware, micro codes, circuits, data, a database, data structures, tables, arrays, or variables.

Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Hereinafter, embodiments of the present disclosure will be described with reference to accompanying drawings.

FIG. 1A is a perspective view of a display device DD according to an embodiment of the present disclosure.

Referring to FIG. 1A, the display device DD may be a device activated in response to electrical signals. The display device DD may include various embodiments that provide images to various users. For example, the display device DD may be applied to a large-sized electronic item, such as a television set or an outdoor billboard, and a small and medium-sized electronic item, such as a monitor, a mobile phone, a tablet computer, a car navigation unit, and a game unit. These are merely examples, and thus, the display device DD may be applied to other electronic items as long as they do not depart from the concept of the present disclosure.

The display device DD may have a rectangular shape with long sides extending in a first direction DR1 and short sides extending in a second direction DR2 crossing the first direction DR1. However, the shape of the display device DD should not be limited to the rectangular shape, and the display device DD may have a variety of shapes, such as a circular shape, a polygonal shape, etc.

The display device DD may display an image through a display surface DS that is substantially parallel to a plane defined by the first direction DR1 and the second direction DR2 toward a third direction DR3. The third direction DR3 may be substantially parallel to a normal line direction of the display surface DS. The display surface DS through which the image is displayed may correspond to a front surface of the display device DD. The image may include a video and a still image.

In the present embodiment, front (or upper) and rear (or lower) surfaces of each member or each unit of the display device DD may be defined with respect to a direction in which the image is displayed. The front and rear surfaces may be opposite to each other in the third direction DR3, and a normal line direction of each of the front and rear surfaces may be substantially parallel to the third direction DR3. A separation distance between the front surface and the rear surface in the third direction DR3 may correspond to a thickness or a height of each member (or each unit) in the third direction DR3. In the present disclosure, the expression "when viewed in a plane" may mean a state of being viewed in the third direction DR3. In the present disclosure, the expression "when viewed in a cross-section" may mean a state of being viewed in the first direction DR1 or the second direction DR2. Meanwhile, directions indicated by the first, second, and third directions DR1, DR2, and DR3 may be relative to each other, and thus, the directions indicated by the first, second, and third directions DR1, DR2, and DR3 may be changed to other directions.

FIG. 1A shows the display device DD with a flat display surface DS that is flat as a representative example, however, the display surface DS of the display device DD should not be limited thereto or thereby. According to an embodiment, the display surface DS may have a curved shape or a three-dimensional shape.

The display device DD may be flexible. The term "flexible" used herein refers to the property of being able to be bent, and the flexible display device may include all structures from a structure that is completely bent to a structure that is bent at the scale of a few nanometers. As an example, the flexible display device DD may be a curved device or a foldable device. However, the display device DD should not be limited to the flexible display device, and the display device DD may be rigid.

The display surface DS of the display device DD may include a display area DA and a non-display area NDA. The display area DA may be an area through which the image is displayed in the display device DD, and the user may perceive the image through the display area DA. In the present embodiment, the display area DA may have a rectangular shape, but the display area DA may have a variety of shapes.

The non-display area NDA may be an area through which the image is not displayed in the display device DD. The non-display area NDA may have a predetermined color and may block a light. The non-display area NDA may be defined adjacent to the display area DA. As an example, the non-display area NDA may be defined outside the display area DA and may surround the display area DA, however, this is merely an example. According to an embodiment, the non-display area NDA may be defined adjacent to only one side of the display area DA, may be defined in a side surface rather than the front surface of the display device DD, or may be omitted.

The display device DD may include a folding area FA and a plurality of non-folding areas NFA1 and NFA2. The folding area FA may be referred to as a foldable area, and the non-folding areas NFA1 and NFA2 may be referred to as non-foldable areas.

The non-folding areas NFA1 and NFA2 may include a first non-folding area NFA1 and a second non-folding area NFA2. The folding area FA may be disposed between the first non-folding area NFA1 and the second non-folding area NFA2. The first non-folding area NFA1, the folding area FA, and the second non-folding area NFA2 may be sequentially arranged in the display device DD along a direction opposite to the first direction DR1.

The display device DD may be folded with respect to a folding axis (not shown) substantially parallel to the short sides thereof. When the display device DD is folded, the first non-folding area NFA1 and the second non-folding area NFA2 may face each other, and the second non-folding area NFA2 may overlap a portion of the first non-folding area NFA1 in a plan view. Here, the "plan view" may be defined as a view in the third direction DR3, like FIG. 6.

The display device DD may include a housing HS and a window WM to provide an exterior thereof. A display layer, a sensor layer, and an optical film, which form the display device DD, may be disposed in a space between the housing HS and the window WM.

The window WM may include an optically transparent insulating material. As an example, the window WM may include a glass or plastic material. The window WM may have a single-layer or multi-layer structure. As an example, the window WM may include a plurality of plastic films attached to each other by an adhesive or a glass substrate and a plastic film attached to the glass substrate by an adhesive.

The window WM may have various sizes depending on its type. As an example, the window WM may have a size within a range from about 6.7 inches to about 8 inches.

The window WM may include a window folding area WFA, a first window non-folding area WNFA1, and a second window non-folding area WNFA2. The window folding area WFA may be disposed between the first window non-folding area WNFA1 and the second window non-folding area WNFA2. The first window non-folding area WNFA1, the window folding area WFA, and the second window non-folding area WNFA2 may be sequentially defined in the display device DD along the direction opposite to the first direction DR1. That is, the first window non-folding area WNFA1 may overlap the first non-folding area NFA1, the window folding area WFA may overlap the folding area FA, and the second window non-folding area WNFA2 may overlap the second non-folding area NFA2 in a plan view.

Figure 1B:
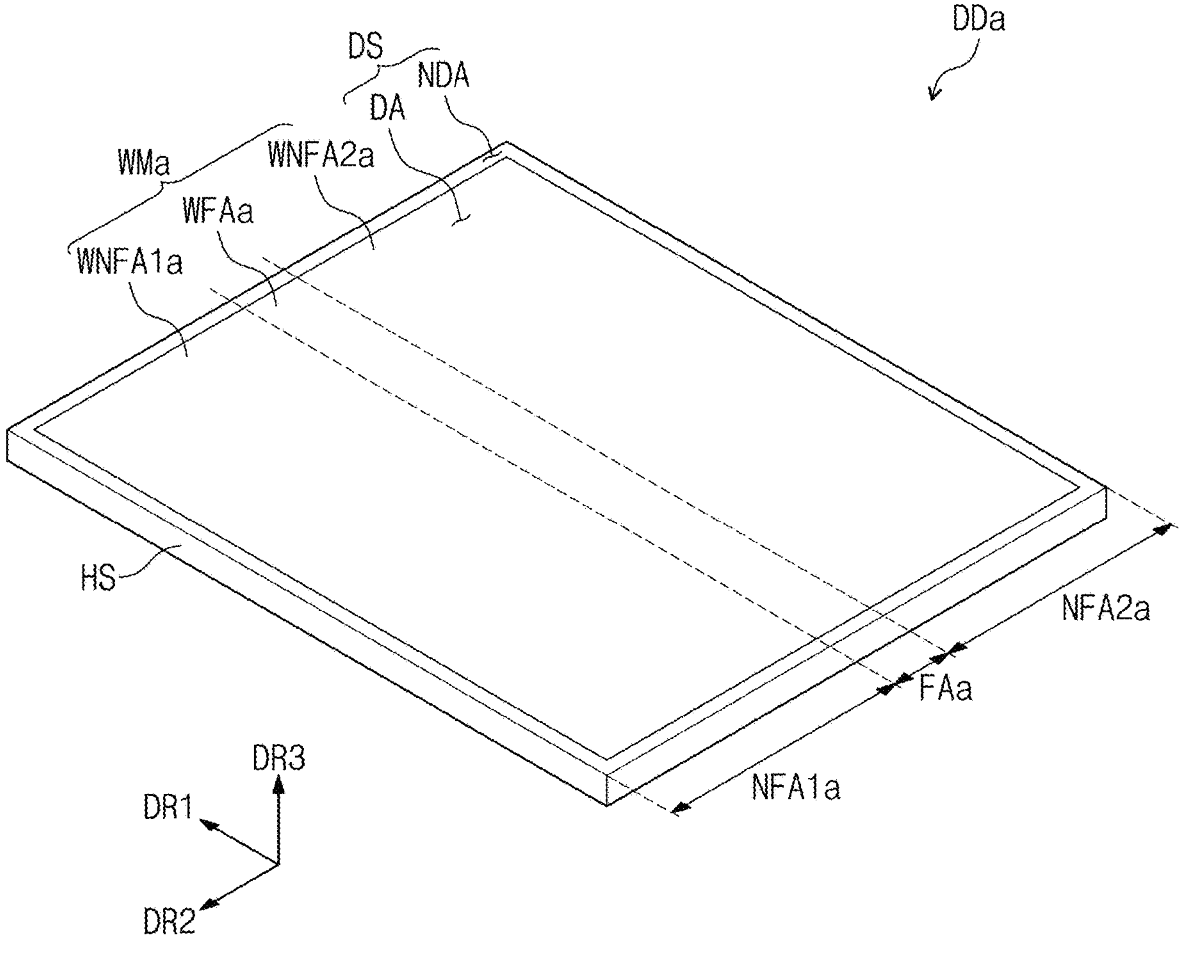
FIG. 1B is a perspective view of a display device according to an embodiment of the present disclosure.

FIG. 1B is a perspective view of a display device DDa according to an embodiment of the present disclosure. In FIG. 1B, the same reference numerals denote the same elements in FIG. 1A, and thus, detailed descriptions of the same elements will be omitted.

The display device DDa may include a folding area FAa and a plurality of non-folding areas NFA1*a* and NFA2*a*. The folding area FAa may be referred to as a foldable area, and the non-folding areas NFA1*a* and NFA2*a* may be referred to as non-foldable areas.

The non-folding areas NFA1*a* and NFA2*a* may include a first non-folding area NFA1*a* and a second non-folding area NFA2*a*. The folding area FAa may be defined between the first non-folding area NFA1*a* and the second non-folding area NFA2*a*. The first non-folding area NFA1*a*, the folding area FAa, and the second non-folding area NFA2*a* may be sequentially arranged in the display device DD along a direction opposite to the second direction DR2.

The display device DDa may be folded with respect to a folding axis (not shown) substantially parallel to long sides thereof. When the display device DDa is folded, the first non-folding area NFA1*a* and the second non-folding area NFA2*a* may face each other, and the second non-folding area NFA2*a* may overlap a portion of the first non-folding area NFA1*a* in a plan view.

A window WMa may include a window folding area WFAa, a first window non-folding area WNFA1*a*, and a second window non-folding area WNFA2*a*. The window folding area WFAa may be defined between the first window non-folding area WNFA1*a* and the second window non-folding area WNFA2*a*. The first window non-folding area WNFA1*a*, the window folding area WFAa, and the second window non-folding area WNFA2*a* may be sequentially arranged in the display device DDa along the direction opposite to the second direction DR2. That is, the first window non-folding area WNFA1*a* may overlap the first non-folding area NFA1*a*, the window folding area WFAa may overlap the folding area FAa, and the second window non-folding area WNFA2*a* may overlap the second non-folding area NFA2*a* in a plan view.

Figure 2:
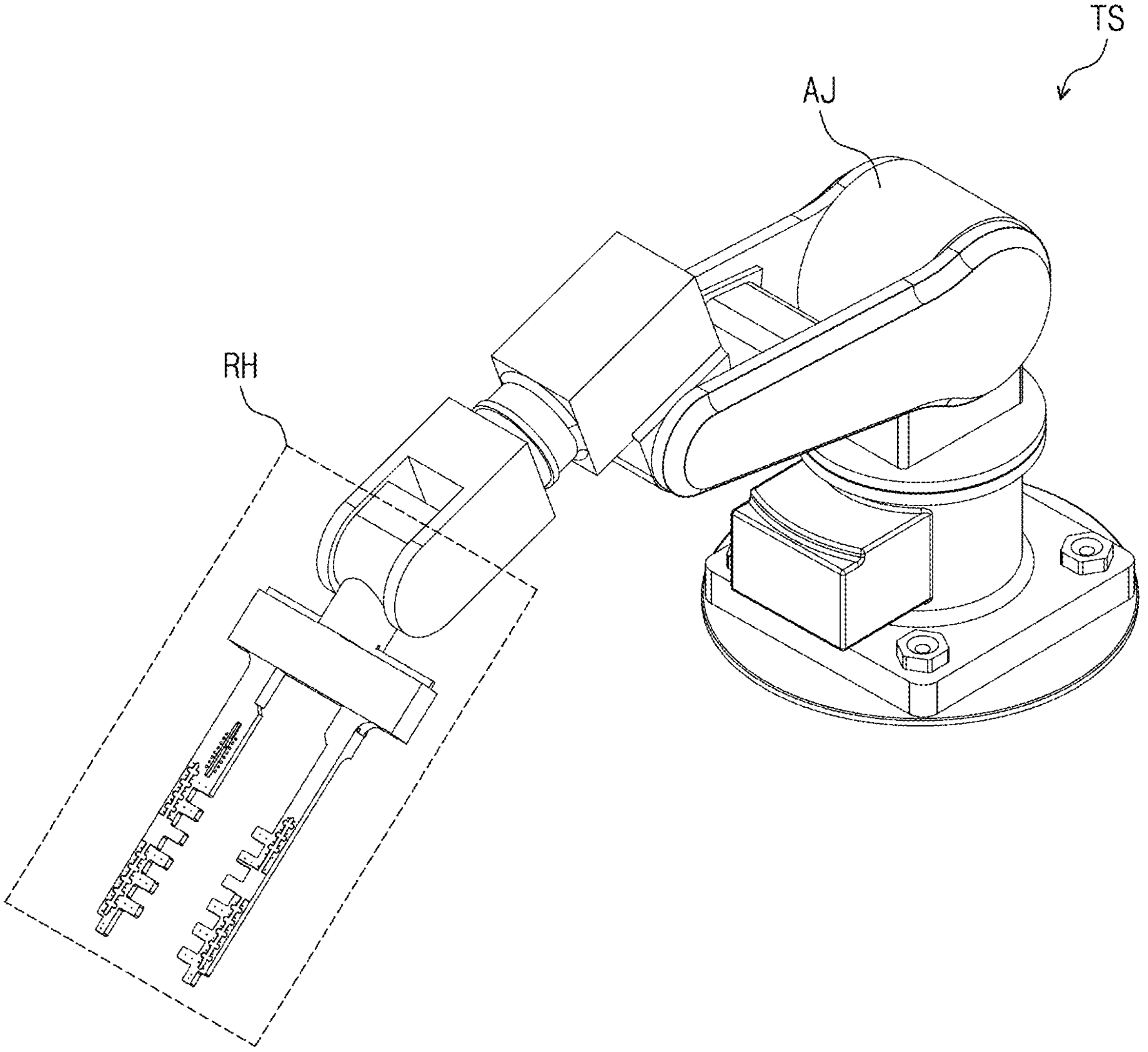
FIG. 2 is a perspective view of a transfer apparatus according to an embodiment of the present disclosure.

FIG. 2 is a perspective view of a transfer apparatus TS according to an embodiment of the present disclosure.

Referring to FIG. 2, the transfer apparatus TS may include a robot arm RH and a joint part AJ. The transfer apparatus TS may adhere the window WM (refer to FIG. 1A) to the robot arm RH by suction and may transfer the window WM (refer to FIG. 1A).

The window WM, which is a transfer target, may have various sizes. Since the thickness of the window WM is thin, the window WM may be sagged, layers of the window WM may be delaminated, or other defects in appearance may occur on the window WM during the transfer process. Accordingly, a separate robot arm RH is desirable for each size of the window WM to prevent the above defects from occurring.

According to an embodiment, windows of various sizes may be transferred by adjusting a distance between first and second hands constituting the robot arm RH without replacing the robot arm RH. In this case, there is no need to replace the robot arm RH even though the size of the window WM is changed. Accordingly, a process to replace the robot arm RH, a place to store a robot arm to replace the robot arm RH, and a manpower to replace the robot arm RH may not be necessary. In addition, a window evaluation sample used to test the replaced robot arm RH may also not be necessary. Accordingly, when the distance between the first and second hands constituting the robot arm RH is able to be adjusted, a production equipment efficiency may increase, and a replacement cost may not be required.

In addition, according to an embodiment, the robot arm RH may not be in contact with the folding area WFA to prevent a bending strength of the folding area WFA (refer to FIG. 1A) of the window WM from being lowered.

Figure 3:
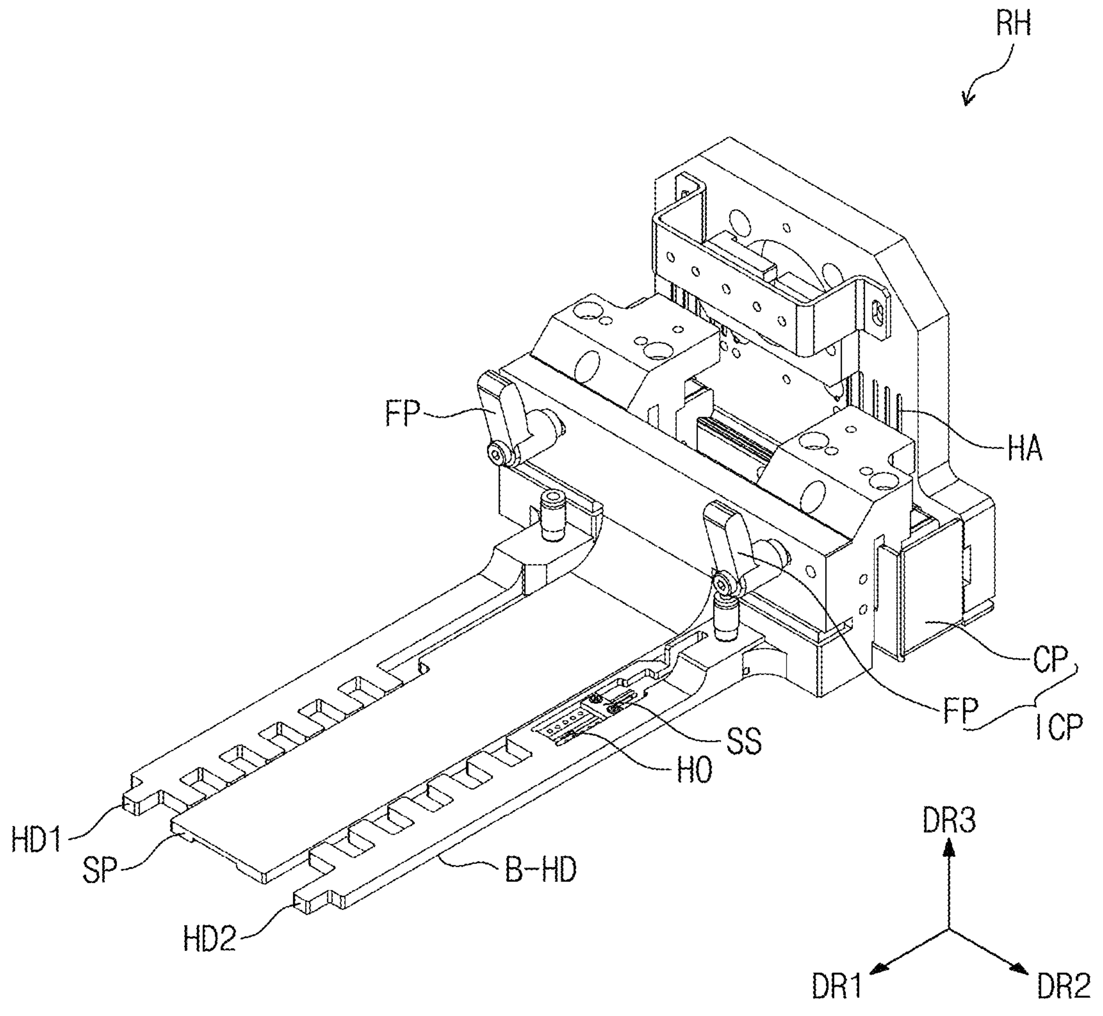
FIG. 3 is a perspective view of a robot arm according to an embodiment of the present disclosure.
Figure 4:
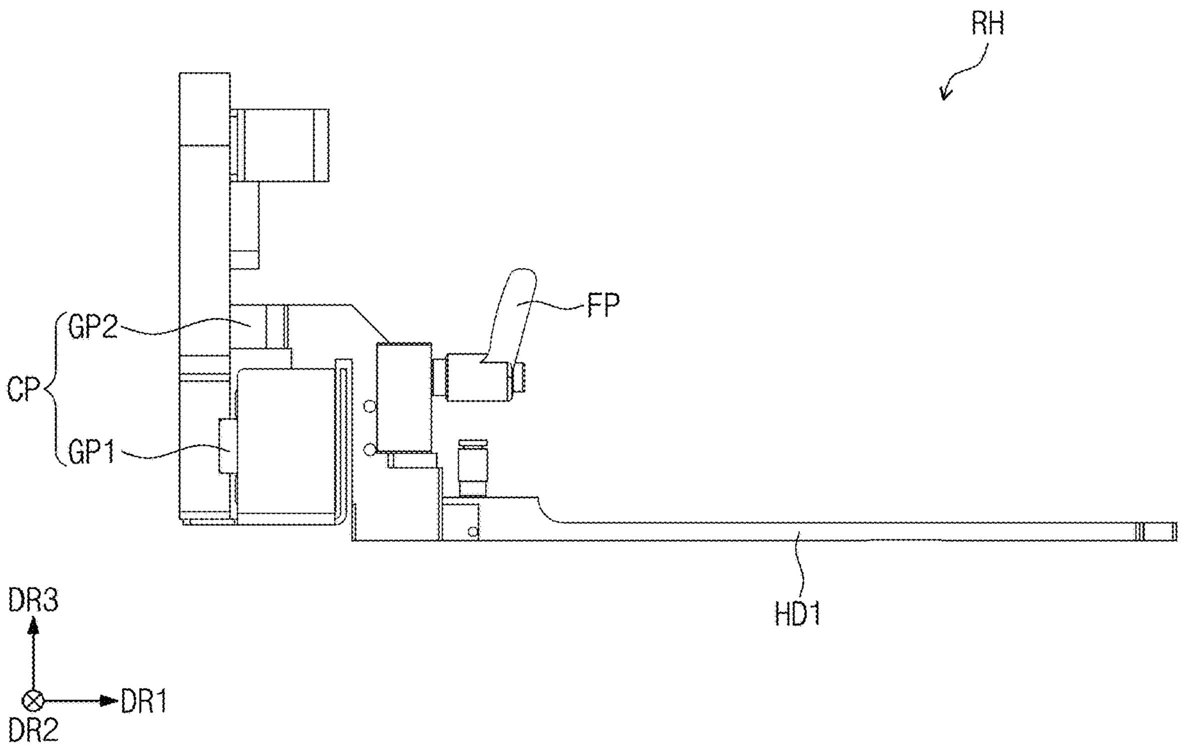
FIG. 4 is a side view of a robot arm according to an embodiment of the present disclosure.

FIG. 3 is a perspective view of the robot arm RH according to an embodiment of the present disclosure. FIG. 4 is a side view of the robot arm RH according to an embodiment of the present disclosure.

Referring to FIGS. 3 and 4, the robot arm RH may include the first hand HD1, the second hand HD2, a distance adjusting part ICP, and an auxiliary member SP.

Each of the first hand HD1 and the second hand HD2 may extend in the first direction DR1, and the first hand HD1 and the second hand HD2 may be spaced apart from each other in the second direction DR2. A hole HO may be defined through the second hand HD2, and a sensor part SS may be attached to the hole HO. The sensor part SS may sense whether the transfer target is present or not. As an example, the sensor part SS may sense whether the window WM or WMa (refer to FIG. 1A or 1B) is present on a lower surface B-HD of the robot arm RH.

A position of the sensor part SS may be adjusted depending on the size of the window WM or WMa. As an example, the position of the sensor part SS in the hole HO may be changed. As an example, in a case where a relatively small window WM is mounted, the sensor part SS may be provided remotely from the distance adjusting part ICP, and in a case where a relatively large window WMa is mounted, the sensor part SS may be provided adjacent to the distance adjusting part ICP.

The first hand HD1 may move along a direction opposite to the second direction DR2, and the second hand HD2 may move along the second direction DR2. As the first hand HD1 and the second hand HD2 move, the distance between the first hand HD1 and the second hand HD2 may be changed.

The distance adjusting part ICP may adjust the distance between the first hand HD1 and the second hand HD2 in the second direction DR2. The distance adjusting part ICP may include a transfer part CP and a fixing part FP.

The transfer part CP may allow the first hand HD1 and the second hand HD2 to move in a direction substantially parallel to the second direction DR2 to adjust the distance between the first hand HD1 and the second hand HD2. The transfer part CP may include a first guide part GP1 and a second guide part GP2. The second guide part GP2 may be disposed spaced apart from the first guide part GP1. The first hand HD1 and the second hand HD2 may be coupled to both the first guide part GP1 and the second guide part GP2.

The first guide part GP1 may include a rail (not shown). The first hand HD1 and the second hand HD2 may be fixed to the rail and may move in the direction substantially parallel to the second direction DR2. The second guide part GP2 may prevent the first hand HD1 and the second hand HD2 from shaking and distorting when moving and fixing the first hand HD1 and the second hand HD2. FIG. 4 shows a structure in which the transfer part CP includes the first guide part GP1 and the second guide part GP2 as a representative example, however, the present disclosure should not be limited thereto or thereby. As another example, the transfer part CP may include only the first guide part GP1.

The fixing part FP may fix positions of the first hand HD1 and the second hand HD2. The fixing part FP may fix the first hand HD1 and the second hand HD2 via holes HA defined through a rear surface of the transfer part CP. The distance between the first hand HD1 and the second hand HD2 may be adjusted according to a position of the hole HA used to the fix the first and second hands HD1 and HD2. As an example, when each of the first and second hands HD1 and HD2 is fixed via an outermost hole HA, the window WMa (refer to FIG. 1B) with the largest size (e.g., about 8 inches) may be transferred, and when each of the first and second hands HD1 and HD2 is fixed via an innermost hole HA, the window WM (refer to FIG. 1A) with the smallest size (e.g., about 6.7 inches) may be transferred.

The auxiliary member SP may be disposed between the first hand HD1 and the second hand HD2. The auxiliary member SP may be attached to or detached from between the first hand HD1 and the second hand HD2. The auxiliary member SP may include a magnetic material, and the attachment and detachment of the auxiliary member SP may be performed by a magnetic force. As the magnetic material, e.g., a magnet, having the magnetic force is used, attachment and detachment operations of the auxiliary member SP may be simplified. When the first hand HD1 and the second hand HD2 are spaced apart from each other at a minimum distance, the robot arm RH may be used without the auxiliary member SP, and when the distance between the first hand HD1 and the second hand HD2 is equal to or greater than a predetermined distance, the robot arm RH may be used with the auxiliary member SP. As the auxiliary member SP is used, the window WM or WMa may be prevented from sagging, and a loss caused by the sagging of the window WM or WMa may be compensated.

The robot arm RH may include an anodized aluminum. Each of the first hand HD1 and the second hand HD2 may include a coating layer including fluororesin. When the window WM or WMa, which is vulnerable to static electricity, is transferred, cells may be adhered to cells. That is, the windows WM or WMa may be adhered to one another. However, according to the present disclosure, when the first hand HD1 and the second hand HD2 are coated with the fluororesin, the static electricity may be reduced or eliminated, and thus, defects on the window WM or WMa may be prevented.

The window WM or WMa may be coupled to the lower surface B-HD of the first hand HD1 and the second hand HD2 while being transferred. As an example, the window WM or WMa may be suctioned via a plurality of vacuum holes VH1 and VH2 (refer to FIG. 6) defined through the lower surface B-HD of the first hand HD1 and the second hand HD2.

Figure 5:
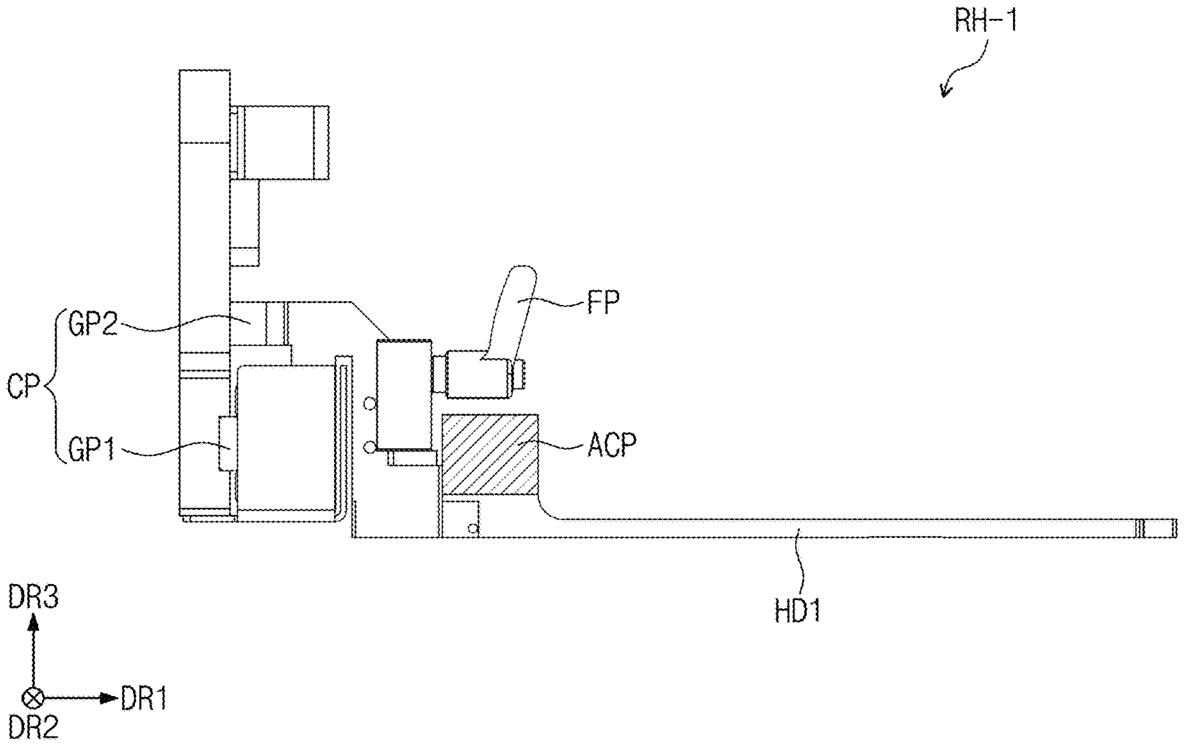
FIG. 5 is a side view of a robot arm according to an embodiment of the present disclosure.

FIG. 5 is a side view of a robot arm RH-1 according to an embodiment of the present disclosure. In FIG. 5, the same reference numerals denote the same elements in FIGS. 3 and 4, and thus, detailed descriptions of the same elements will be omitted.

Referring to FIG. 5, the robot arm RH-1 may further include a foreign substance cover member ACP. The foreign substance cover member ACP may be disposed between a first hand HD1 and a distance adjusting part ICP (refer to FIG. 3) and between a second hand HD2 (refer to FIG. 3) and the distance adjusting part ICP (refer to FIG. 3). The foreign substance cover member ACP may prevent a foreign substance generated due to a movement of the first hand HD1 and the second hand HD2 from being provided on the window WM or WMa. The foreign substance cover member ACP may be attachable and detachable.

Figure 6:
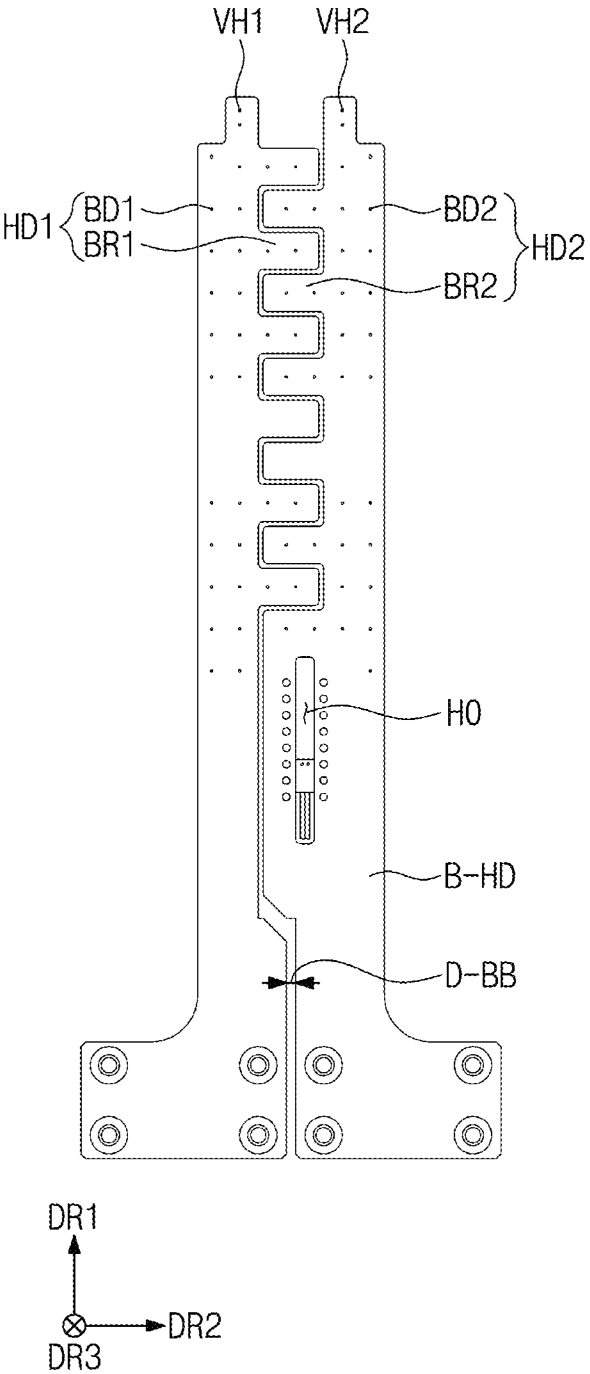
FIGS. 6 to 8 are views showing operations of first and second hands according to an embodiment of the present disclosure.
Figure 7A:
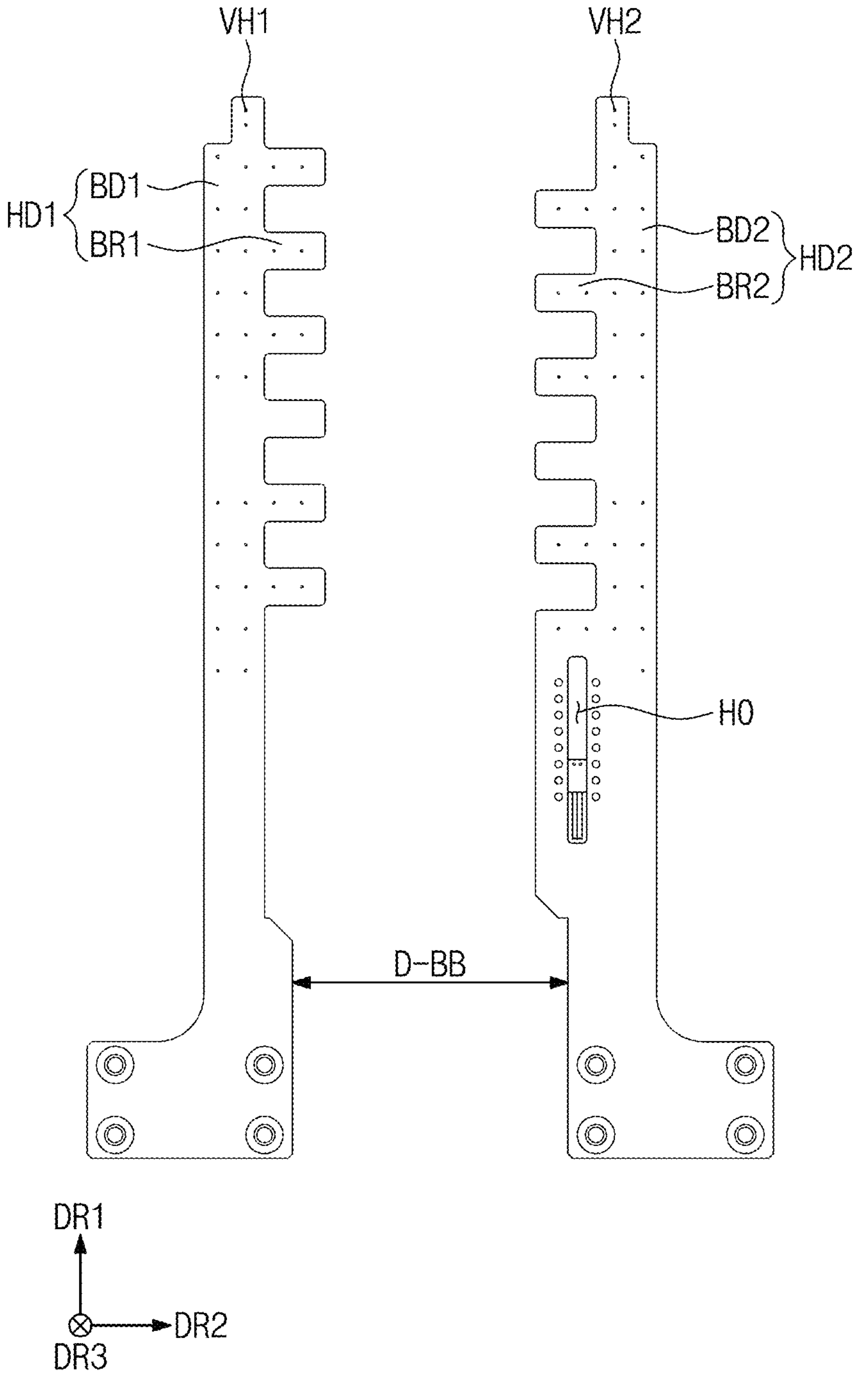
Figure 7B:
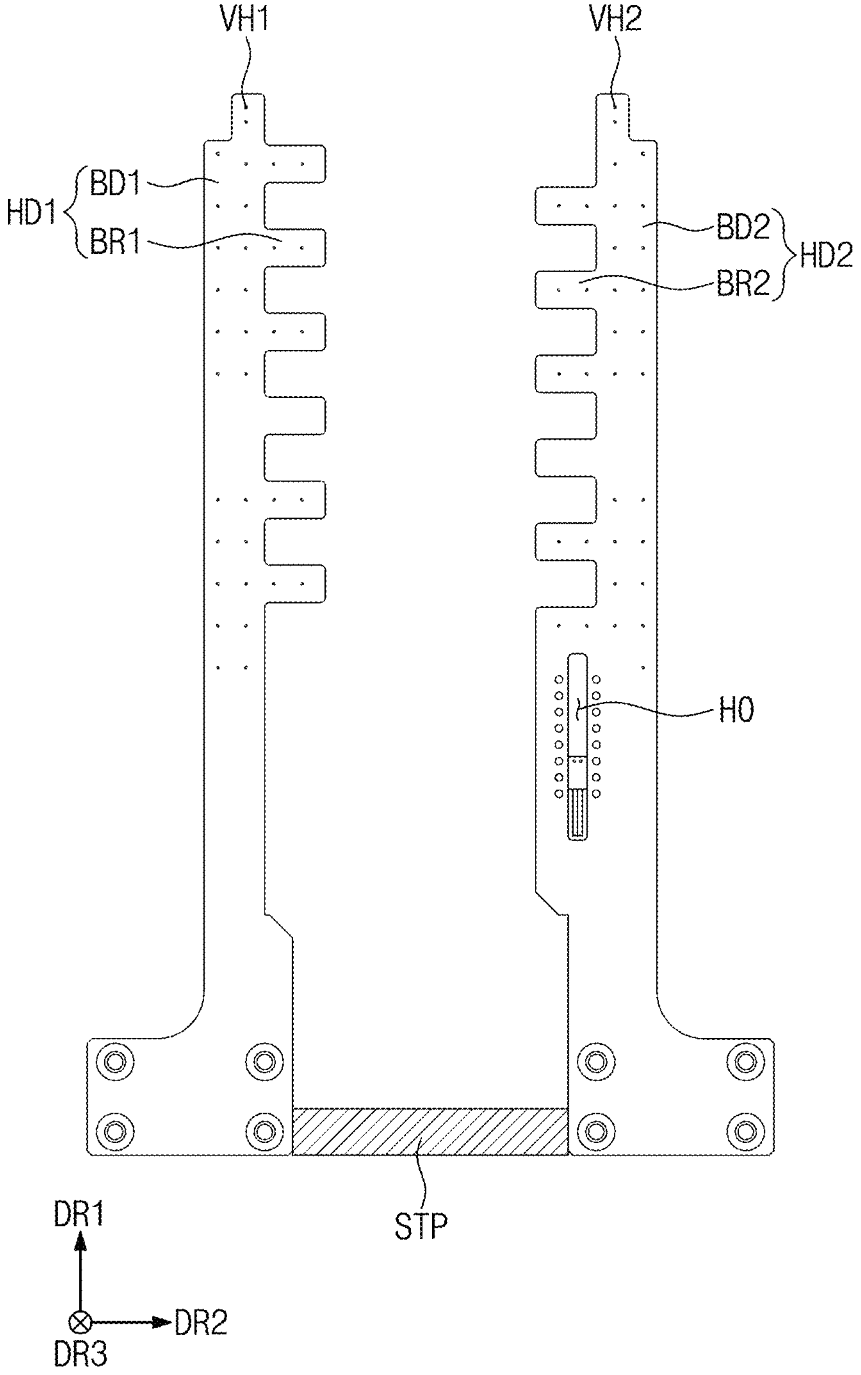
Figure 8:
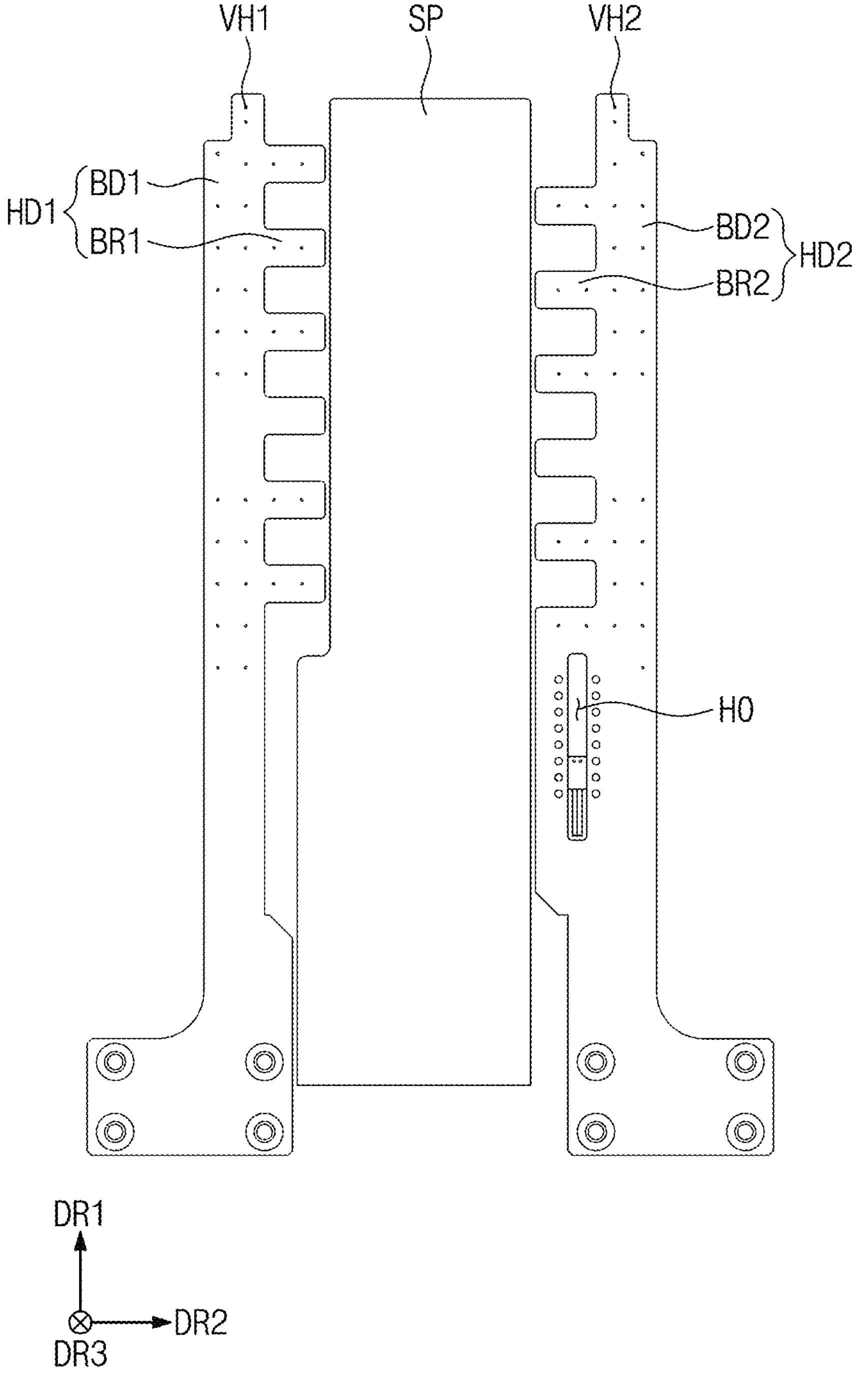

FIGS. 6 to 8 are views showing operations of the first and second hands HD1 and HD2 according to an embodiment of the present disclosure. FIG. 6 is a view from a bottom of the first and second hands HD1 and HD2.

Referring to FIG. 6, the first hand HD1 may be provided with a plurality of first vacuum holes VH1 defined therethrough, and the second hand HD2 may be provided with a plurality of second vacuum holes VH2 defined therethrough. Due to the first vacuum holes VH1 and the second vacuum holes VH2, the first hand HD1 and the second hand HD2 may suction a transfer target (e.g., window WM or WMa) and may transfer the transfer target. Each of the first vacuum holes VH1 and each of the second vacuum holes VH2 may have a diameter of about 0.5 millimeters (mm). However, this is merely an example, and the number and size of the first and second vacuum holes VH1 and VH2 may be changed.

The first hand HD1 may include a first body portion BD1 and a plurality of first protruding portions BR1. The second hand HD2 may include a second body portion BD2 and a plurality of second protruding portions BR2.

The first body portion BD1 may extend in the first direction DR1. The first protruding portions BR1 may be protruded from the first body portion BD1 to the second direction DR2 crossing the first direction DR1. The first protruding portions BR1 may be disposed between the first body portion BD1 and the second body portion BD2 and may be arranged spaced apart from each other in the first direction DR1.

The second body portion BD2 may extend in the first direction DR1. The hole HO may be defined through the second body portion BD2. The second protruding portions BR2 may be protruded from the second body portion BD2 to the direction opposite to the second direction DR2. The second protruding portions BR2 may be disposed between the first body portion BD1 and the second body portion BD2 and may be arranged spaced apart from each other in the first direction DR1.

When a distance D-BB between the first body portion BD1 and the second body portion BD2 in the second direction DR2 is a minimum distance, the first protruding portions BR1 may be alternately arranged one by one with the second protruding portions BR2 in the first direction DR1.

As shown in FIG. 6, when the distance D-BB between the first body portion BD1 and the second body portion BD2 is the minimum distance, the robot arm RH may transfer the relatively small window WM (refer to FIG. 1). In this case, the window WM may have the smallest size (e.g., about 6.7 inches). Even though FIG. 6 shows an embodiment that when a distance D-BB between the first body portion BD1 and the second body portion BD2 in the second direction DR2 is a minimum distance, the first protruding portions BR1 may be alternately arranged one by one with the second protruding portions BR2 in the first direction DR1, the shapes of the first protruding portions BR1 and the second protruding portions BR2 should not be limited thereto or thereby. Any shapes, for example, a case that the extending direction of the first protruding portions BR1 crosses the extending direction of the second protruding portions BR2, may be possible of the first protruding portions BR1 and the second protruding portions BR2 if the shapes may allow to hold the auxiliary member SP therebetween.

Referring to FIGS. 7A and 7B, the distance D-BB between the first body portion BD1 and the second body portion BD2 may be greater than the minimum distance by adjusting the distance between the first hand HD1 and the second hand HD2. The distance adjusting part ICP (refer to FIG. 3) may adjust the distance D-BB using a setting member STP that provides a reference for the distance D-BB between the first hand HD1 and the second hand HD2. The setting member STP may have a shape extending in the second direction DR2 and may be disposed between the first hand HD1 and the second hand HD2. The setting member STP may be attachable and detachable to and from the first hand HD1 and the second hand HD2, and may be used to set the distance between the first hand HD1 and the second hand HD2 when the distance D-BB between the first hand HD1 and the second hand HD2 is adjusted for each size of the window WM or WMa (refer to FIGS. 1A and 1B) to be transferred. The setting member STP may be provided for each size of the window WM or WMa.

Referring to FIG. 7A, the window WM or WMa may be transferred after the setting member STP is removed and the distance D-BB between the first hand HD1 and second hand HD2 is widened. The window WM or WMa may be transferred without the auxiliary member SP between the first hand HD1 and the second hand HD2. In this case, the size of the window WM or WMa, which does not sag, may be equal to or greater than about the smallest size (e.g., 6.7 inches) and equal to or smaller than a middle size (e.g., about 7.7 inches).

Referring to FIG. 8, the first hand HD1 and the second hand HD2 may move further in a direction substantially parallel to the second direction DR2, and thus, the distance D-BB between the first hand HD1 and the second hand HD2 may increase. The auxiliary member SP may be inserted into a space between the first hand HD1 and the second hand HD2, and thus, the window WMa (refer to FIG. 1B) may be prevented from sagging while being transferred. In this case, the size of the window WMa may be equal to or greater than a middle size (e.g., about 7.7 inches).

According to the present disclosure, since there is no need to replace the robot arm RH, an additional manufacturing cost of the robot arm RH may be reduced, and a time required for the additional manufacturing of the robot arm RH may be reduced. As a result, the efficiency of production equipment may increase.

Figure 9A:
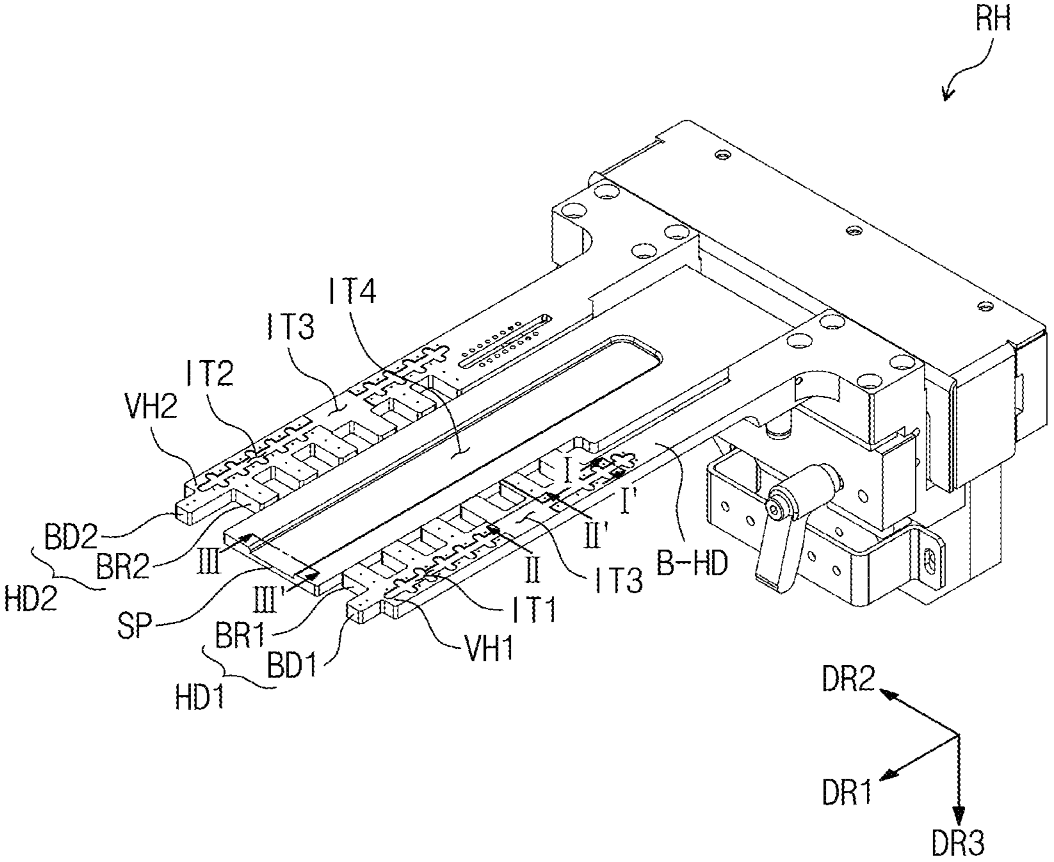
FIG. 9A is a perspective view of a lower surface of the first and second hands according to an embodiment of the present disclosure.

FIG. 9A is a perspective view of the lower surface B-HD of the first and second hands HD1 and HD2 according to an embodiment of the present disclosure.

Referring to FIG. 9A, the window WM or WMa (refer to FIG. 1A or 1B) may be coupled to the lower surface B-HD of the first hand HD1 and the second hand HD2 and may be transferred. As an example, the window WM or WMa may be suctioned to the lower surface B-HD of the first hand HD1 and the second hand HD2 using the vacuum holes VH1 and VH2 that are defined in the lower surface B-HD of the first hand HD1 and the second hand HD2, respectively.

First, second, third, and fourth engraved patterns IT1, IT2, IT3, and IT4 may be defined in the robot arm RH. The first engraved pattern IT1 may be defined in the first body portion BD1. The first engraved pattern IT1 may not overlap the first vacuum holes VH1 in a plan view and may extend in the first direction DR1. The second engraved pattern IT2 may be defined in the second body portion BD2. The second engraved pattern IT2 may not overlap the second vacuum holes VH2 in a plan view and may extend in the first direction DR1. The first engraved pattern IT1 and the second engraved pattern IT2 may discharge a residual pressure generated in the process of vacuum suctioning using the vacuum holes VH1 and VH2, and thus may minimize a vacuum non-separation phenomenon (i.e., a phenomenon that the window is not separated from the robot arm even after the suction stops). In addition, a contact portion (i.e., total contact area) between the window WM or WMa and the robot arm RH may be reduced, and thus, the static electricity may also be reduced. Accordingly, defects such as cracks may be reduced in the window WM or WMa.

The third engraved pattern IT3 may be defined in the first hand HD1 and the second hand HD2. The third engraved pattern IT3 may not overlap the first vacuum holes VH1 and the second vacuum holes VH2 in a plan view and may extend in the second direction DR2. The third engraved pattern IT3 may correspond to the folding area WFA (refer to FIG. 1A) of the window WM (refer to FIG. 1A). Since the third engraved pattern IT3 is formed, the folding area WFA of the window WM may not be in contact with the first hand HD1 and the second hand HD2 when the window WM is transferred. Accordingly, defects by the contact may be reduced or prevented in the folding area WFA of the window WM. In this case, the window WM may be disposed to be folded along an axis parallel to the second direction DR2.

The fourth engraved pattern IT4 may be defined in the auxiliary member SP. The fourth engraved pattern IT4 may extend in the first direction DR1. The fourth engraved pattern IT4 may correspond to the folding area WFAa (refer to FIG. 1B) of the window WMa (refer to FIG. 1B). Since the fourth engraved pattern IT4 is formed, the folding area WFAa of the window WMa may not be in contact with the auxiliary member SP when the window WMa is transferred. Accordingly, defects may be reduced or prevented in the folding area WFAa of the window WMa. In this case, the window WMa may be disposed to be folded along an axis parallel to the first direction DR1.

A portion of each of the first hand HD1 and the second hand HD2, which overlap the first, second, and third engraved patterns IT1, IT2, and IT3 in a plan view, may have a thickness in the third direction DR3 different from a thickness of the other portion of each of the first hand HD1 and the second hand HD2, which do not overlap the first, second, and third engraved patterns IT1, IT2, and IT3. The thickness of the portion of each of the first hand HD1 and the second hand HD2, which overlap the first, second, and third engraved patterns IT1, IT2, and IT3, may be smaller than the thickness of the other portion of each of the first hand HD1 and the second hand HD2, which do not overlap the first, second, and third engraved patterns IT1, IT2, and IT3.

According to the present disclosure, when the window WM or WMa is transferred, the transfer apparatus may be prevented from being physically in contact with a predetermined portion of the window WM or WMa, and thus, the defects of the window WM or WMa of the foldable display device may be reduced.

Figure 9B:
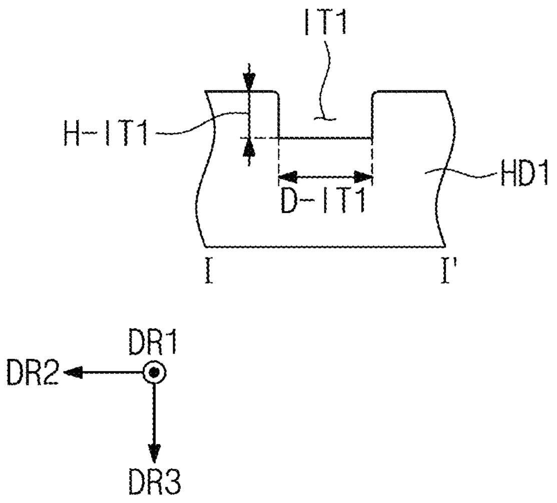
FIG. 9B is a cross-sectional view of a robot arm taken along a line I-I' of FIG. 9A according to an embodiment of the present disclosure.
Figure 9C:
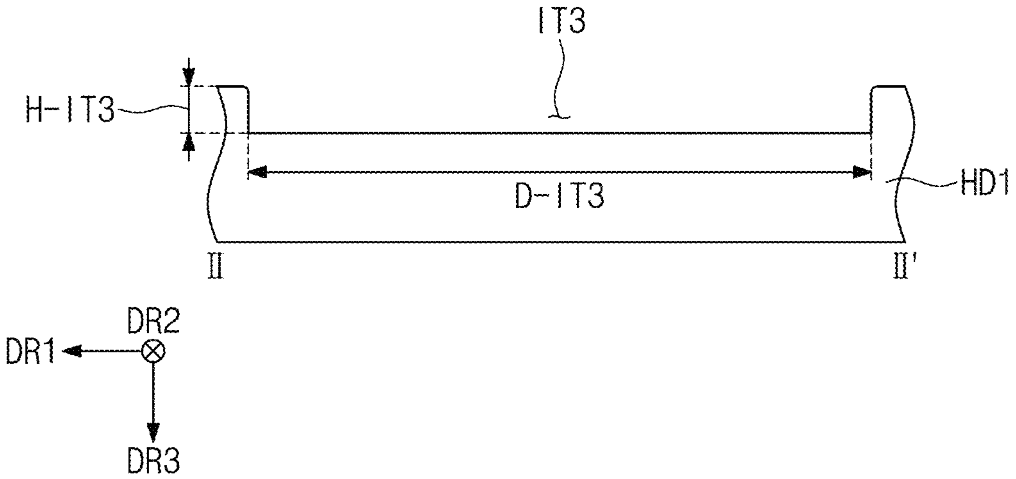
FIG. 9C is a cross-sectional view of a robot arm taken along a line II-II' of FIG. 9A according to an embodiment of the present disclosure.
Figure 9D:
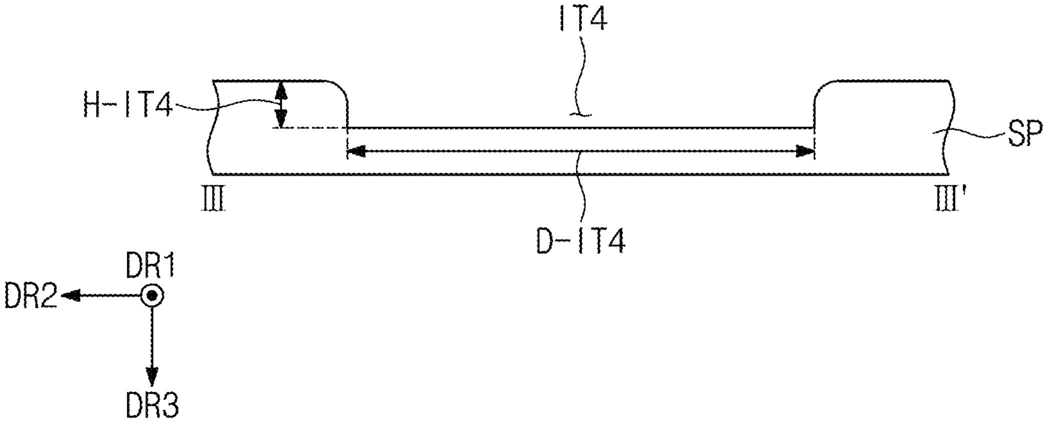
FIG. 9D is a cross-sectional view of a robot arm taken along a line III-III' of FIG. 9A according to an embodiment of the present disclosure.

FIG. 9B is a cross-sectional view of the robot arm RH taken along a line I-I' of FIG. 9A according to an embodiment of the present disclosure. FIG. 9C is a cross-sectional view of the robot arm RH taken along a line II-II' of FIG. 9A according to an embodiment of the present disclosure. FIG. 9D is a cross-sectional view of the robot arm RH taken along a line III-III' of FIG. 9A according to an embodiment of the present disclosure.

Referring to FIG. 9B, the portion of the first hand HD1, which overlaps the first engraved pattern IT1, may have a thickness different from the thickness of the other portion of the first hand HD1, which does not overlap the first engraved pattern IT1. As an example, the first engraved pattern IT1 may have a depth H-IT1 of about 0.2 mm in the third direction DR3. In addition, in an embodiment, a width D-IT1 in the second direction DR2 of the first engraved pattern IT1 may be about 3 mm. Descriptions on the depth H-IT1 and the width D-IT1 of the first engraved pattern IT1 may be applied to the second engraved pattern IT2 shown in FIG. 9A.

Referring to FIG. 9C, the portion of the first hand HD1, which overlaps the third engraved pattern IT3 in a plan view, may have a thickness different from the thickness of the other portion of the first hand HD1, which does not overlap the third engraved pattern IT3. As an example, a depth H-IT3 of the third engraved pattern IT3 in the third direction DR3 may be about 0.2 mm. In addition, for example, a width D-IT3 in the first direction DR1 of the third engraved pattern IT3 may be about 20 mm. Descriptions on the depth H-IT3 and the width D-IT3 of the third engraved pattern IT3 may be applied to the second hand HD2.

Referring to FIG. 9D, the portion of the auxiliary member SP, which overlaps the fourth engraved pattern IT4 in a plan view, may have a thickness different from the thickness of the other portion of the auxiliary member SP, which does not overlap the fourth engraved pattern IT4. As an example, a depth H-IT4 of the fourth engraved pattern IT4 in the third direction DR3 may be about 0.2 mm. In addition, for example, a width D-IT4 in the second direction DR2 of the fourth engraved pattern IT4 may be about 20 mm.

FIGS. 9B to 9D show the thickness and the width of the first, second, third, and fourth engraved patterns IT1, IT2, IT3, and IT4 as a representative example, however, they should not be limited thereto or thereby. The shape, size, position, and number of the first, second, third, and fourth engraved patterns IT1, IT2, IT3, and IT4 may be changed depending on the size and shape of the window WM or WMa.

Figure 10:
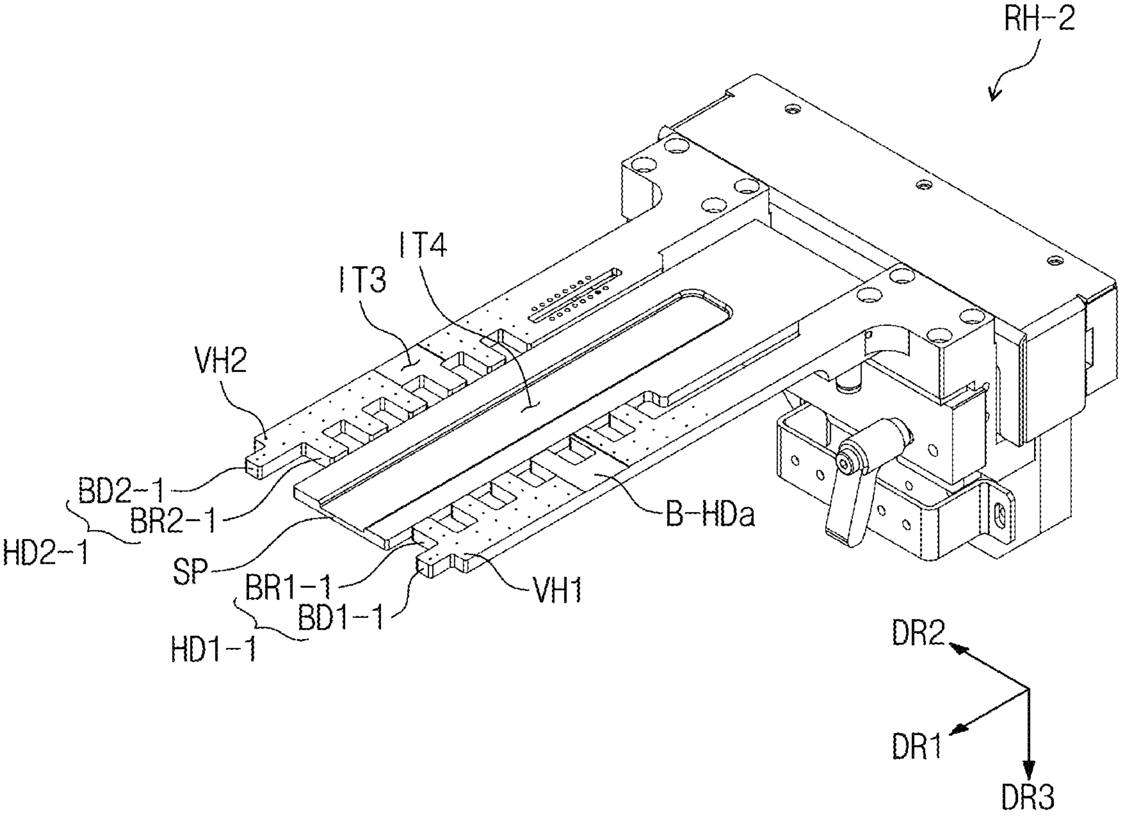
FIG. 10 is a perspective view of a lower surface of the first and second hands according to another embodiment of the present disclosure.

FIG. 10 is a view of a lower surface B-HDa of a first hand HD1-1 and a second hand HD2-1 according to another embodiment of the present embodiment. In FIG. 10, the same reference numerals denote the same elements in FIG. 9A, and thus, detailed descriptions of the same elements will be omitted.

Referring to FIG. 10, a robot arm RH-2 may have a structure obtained by removing the first and second engraved patterns IT1 and IT2 (refer to FIG. 9A) from the robot arm RH shown in FIG. 9A. The first hand HD1-1 and the second hand HD2-1 may not include the first and second engraved patterns IT1 and IT2 and may include a third engraved pattern IT3. An auxiliary member SP may include a fourth engraved pattern IT4. According to the present disclosure, the folding area WFA or WFAa (refer to FIG. 1A or 1B) of the window WM or WMa (refer to FIG. 1A or 1B) may not be in contact with the first hand HD1-1 and the second hand HD2-1 when the window WM or WMa (refer to FIG. 1A or 1B) is transferred. Accordingly, defects in the folding area WFA or WFAa of the window WM or WMa may be reduced or prevented.

Although the embodiments of the present disclosure have been described, it is understood that the present disclosure should not be limited to these embodiments but various changes and modifications can be made by one ordinary skilled in the art within the spirit and scope of the present disclosure as hereinafter claimed. Therefore, the disclosed subject matter should not be limited to any single embodiment described herein, and the scope of the present invention shall be determined according to the attached claims.

What is claimed is:

1. A robot arm comprising:

a first hand comprising a first body portion extending in a first direction and a plurality of first protruding portions protruded from the first body portion to a second direction crossing the first direction, wherein the plurality of first protruding portions overlap the first body portion when viewed in the second direction, and are arranged spaced apart from each other in the first direction;

a second hand comprising a second body portion extending in the first direction and a plurality of second protruding portions protruded from the second body portion to the second direction, wherein the plurality of second protruding portions overlap the second body portion when viewed in the second direction, and are arranged spaced apart from each other in the first direction; and a distance adjusting part, which adjusts a distance between the first hand and the second hand, wherein the first protruding portions and the second protruding portions are disposed between the first body portion and the second body portion.

2. The robot arm of claim 1, wherein the first protruding portions are alternately arranged one by one with the second protruding portions in the first direction when the distance between the first body portion and the second body portion is a minimum distance.

3. The robot arm of claim 1, wherein the first hand defines a plurality of first vacuum holes therein, and the second hand defines a plurality of second vacuum holes therein.

4. The robot arm of claim 3, wherein the first body portion comprises a first engraved pattern that is defined therein, the first engraved pattern does not overlap the first vacuum holes in a plan view, and extends in the first direction, the second body portion comprises a second engraved pattern that is defined therein, and the second engraved pattern does not overlap the second vacuum holes in the plan view, and extends in the first direction.

5. The robot arm of claim 4, wherein each of the first hand and the second hand comprises a third engraved pattern that is defined therein, and the third engraved pattern does not overlap the first vacuum holes and the second vacuum holes in the plan view, and extends in the second direction.

6. The robot arm of claim 5, wherein the third engraved pattern has a width of about 20 millimeters (mm) in the first direction.

7. The robot arm of claim 5, wherein each of first portions of the first hand and the second hand that overlaps the first, second, and third engraved patterns in the plan view has a thickness different from a thickness of each of second portions of the first hand and the second hand that does not overlap the first, second, and third engraved patterns in the plan view.

8. The robot arm of claim 1, further comprising an auxiliary member disposed between the first hand and the second hand.

9. The robot arm of claim 8, wherein the auxiliary member comprises a magnetic material, and the auxiliary member is attachable to and detachable from the first hand and the second hand.

10. The robot arm of claim 8, wherein the auxiliary member comprises a fourth engraved pattern defined therein and extending in the first direction.

11. The robot arm of claim 10, wherein the fourth engraved pattern has a width of about 20 mm in the second direction.

12. The robot arm of claim 1, wherein the distance adjusting part comprises:

a transfer part, which adjusts the distance between the first hand and the second hand; and a fixing part, which fixes a position of the first hand and a position of the second hand.

13. The robot arm of claim 12, wherein the distance adjusting part further comprises a setting member, which provides a reference of the distance between the first hand and the second hand, and the setting member is attachable and detachable.

14. The robot arm of claim 12, wherein the transfer part comprises a first guide part and a second guide part spaced apart from the first guide part, and the first hand and the second hand are coupled to the first guide part and the second guide part.

15. The robot arm of claim 1, wherein each of the first hand and the second hand comprises a coating layer comprising a fluororesin.

16. The robot arm of claim 1, further comprising a sensor part disposed to overlap a hole defined through the second hand and which senses a transfer target.

17. The robot arm of claim 1, further comprising a foreign substance cover member disposed between the first hand and the distance adjusting part and between the second hand and the distance adjusting part.

18. A transfer apparatus comprising:

a robot arm, which vacuum-suctions a window; and a joint part connected to the robot arm, the robot arm comprising:

a first hand comprising a first body portion extending in a first direction and a plurality of first protruding portions protruded from the first body portion to a second direction crossing the first direction and arranged in the first direction;

a second hand comprising a second body portion extending in the first direction and a plurality of second protruding portions protruded from the second body portion to the second direction and arranged in the first direction; and a distance adjusting part, which adjusts a distance between the first hand and the second hand, wherein the first protruding portions and the second protruding portions are disposed between the first body portion and the second body portion.

19. The transfer apparatus of claim 18, further comprising an auxiliary member disposed between the first hand and the second hand.

20. The transfer apparatus of claim 19, wherein the first body portion comprises a first engraved pattern that is defined therein, the first engraved pattern does not overlap a plurality of first vacuum holes in a plan view, and extends in the first direction, the second body portion comprises a second engraved pattern that is defined therein, the second engraved pattern does not overlap a plurality of second vacuum holes in the plan view, and extends in the first direction, each of the first hand and the second hand comprises a third engraved pattern that is defined therein, the third engraved pattern does not overlap the first vacuum holes and the second vacuum holes in the plan view, and extends in the second direction, and the auxiliary member comprises a fourth engraved pattern defined therein and extending in the first direction.

* * * * *